United States Patent [19]
Tawada et al.

[11] Patent Number: 6,132,994
[45] Date of Patent: Oct. 17, 2000

[54] LACTOSAMINE OLIGOSACCHARIDES AND METHOD FOR PRODUCING THE SAME

[75] Inventors: Akira Tawada, Sayama; Keiichi Yoshida, Higashimurayama, both of Japan

[73] Assignee: Seikagaku Corporation, Tokyo, Japan

[21] Appl. No.: 09/230,128

[22] PCT Filed: Jul. 23, 1997

[86] PCT No.: PCT/JP97/02551

§ 371 Date: Jan. 22, 1999

§ 102(e) Date: Jan. 22, 1999

[87] PCT Pub. No.: WO98/03524

PCT Pub. Date: Jan. 29, 1998

[30] Foreign Application Priority Data

Jul. 23, 1996 [JP] Japan .................................... 8-193279

[51] Int. Cl.[7] .................................................. C12P 19/26
[52] U.S. Cl. .............................. 435/84; 435/99; 435/100; 435/101; 536/123; 536/123.13; 536/124
[58] Field of Search ................................ 435/84, 99, 100, 435/101; 536/123, 123.13, 124

[56] References Cited

U.S. PATENT DOCUMENTS

| | | |
|---|---|---|
| 4,665,060 | 5/1987 | Mårdh et al. . |
| 4,851,338 | 7/1989 | Mårdh et al. . |
| 5,489,578 | 2/1996 | Rosen et al. . |
| 5,514,660 | 5/1996 | Zopf et al. . |
| 5,580,862 | 12/1996 | Rosen et al. . |
| 5,840,546 | 11/1998 | Morikawa et al. . |
| 5,939,403 | 8/1999 | Maruyama et al. ........................ 514/53 |

FOREIGN PATENT DOCUMENTS

| | | |
|---|---|---|
| 0 344 955 A2 | 12/1989 | European Pat. Off. . |
| 0 765 884 A1 | 4/1997 | European Pat. Off. . |
| 61-47701 | 3/1986 | Japan . |
| 5-230090 | 9/1993 | Japan . |
| 7-62001 | 3/1995 | Japan . |
| WO96/01278 | 1/1996 | WIPO . |
| WO96/16166 | 5/1996 | WIPO . |
| WO 96/16973 | 6/1996 | WIPO . |

OTHER PUBLICATIONS

Fukuda et al, J. Biol. Chem. 251(20):6218–6225, 1976.
Edge et al, J. Biol. Chem. 260(28):15332–15338, 1985.
Sigma Chemical Company Catalogue, p. 33, 1994.
Kiyoshi Nakazawa, et al., Sequential Degradation of Keratan Sulfate by Bacterial Enzymes and Purification of a Sulfatase in the Enzymatic System, The Journal of Biological Chemistry vol. 250, No. 3 Issue of Feb. 10, pp. 905–911, 1975.
Kiyoshi Nakazawa, et al., Purification of Keratan Sulfate–endoglactosidase and Its Action on Keratan Sulfates of Different Origin, The Journal of Biological Chemistry vol. 250, No. 3, Issue of Feb. 10, pp. 912–917, 1975.
Hiroki Nakagawa, et al., Isolation and Characterization of an Endo–β–galactosidase from a New Strain of *Escherichia freundii*, The Journal of Biological Chemistry, vol. 255, No. 12, Issue of Jun. 24, pp. 5955–5959, 1980.
Elizabeth Percival, [41] Desulfation of Polysaccharides, Methods in Carbohydrate Chemistry, vol. VIII, 1980. pp. 281–285.
Kinzo Nagasawa, et al. [42] Desulfation of Glycosaminoglycuronan Sulfates, Methods in Carbohydrate Chemistry, vol. VIII, 1980. pp. 287–289.
Shinichi Hashimoto, et al., Purification of New Keratan Sulfate Degrading Enzyme and Its Property, The Japanese Scientific Journal, vol. 60, No. 8, p. 935, 1988.
Michael Tiemeyer, et al., Carbohydrate ligands for endothelial–leukocyte adhesion molecule 1, Biochemistry vol. 88, pp. 1138–1142, Feb. 1991.
David Tyrrel, et al. Structural requirements for the carbohydrate ligand of E–selection, Biochemistry vol. 88, pp. 10372–10376, Nov. 1991.
Mark R. Stroud, et al. Myeloglycan, a Series of E–Selectin–Binding Polylactosaminolipids Found in Normal Human Leukocytes and Myelocytic Leukemia HL60 Cells, Biochemical and Biophysical Research Communications vol. 209, No.: 3, pp. 777–787, Apr. 26, 1995.
Mark R. Stroud, et al., Monosialogangliosides of Human Myelogenous Leukemia HL60 Cells and Normal Human Leukocytes, 1. Separation of E–Selectin Binding from Nonbinding Gangliosides, and Absence of Sialosyl–Le$^x$ Having Tetraosyl to Octaosyl Core, Biochemistry, 1996, 34, pp. 758–769.
Mark R. Stroud, et al., Monosialogangliosides of Human Myelogenous Leukemia HL60 Cells and Normal Human Leukocytes. 2. Characterization of E–Selectin Binding Fractions, and Structural Requirements for Physiological Binding to E–Selectin.

*Primary Examiner*—Francisco Prats
*Attorney, Agent, or Firm*—Knobbe, Martens, Olson & Bear, LLP

[57] ABSTRACT

A method for producing an N-acetyllactosamine oligosaccharide, comprising the steps of:

adjusting a sulfate group content of keratan sulfate;
  allowing an enzyme having an ability to cleave a glycosidic linkage of keratan sulfate to act on the keratan sulfate with the adjusted sulfate group content to obtain a sulfated N-acetyllactosamine oligosaccharide; and
  completely desulfating said sulfated N-acetyllactosamine oligosaccharide.

14 Claims, 3 Drawing Sheets

LACTOSAMINE OLIGOSACCHARIDES AND METHOD FOR PRODUCING THE SAME

TECHNICAL FIELD

The present invention relates to a novel method for producing an N-acetyllactosamine oligosaccharide and more particularly to a method for producing an N-acetyllactosamine oligosaccharide by enzymatic reaction and chemical reaction from keratan sulfate whose sulfate group content has been adjusted. Also, the present invention relates to a novel method for producing a sulfated N-acetyllactosamine oligosaccharide. Further, the present invention relates to a novel N-acetyllactosamine oligosaccharide.

BACKGROUND ART

Oligosaccharides having an N-acetyllactosamine (LacNAc) structure as their skeleton and derivatives thereof play an important physiological role in vivo as a sugar chain having ability to bind to selectin family compounds. It has been revealed that expression of these sugar chains on cell surfaces participates in specific adhesion between heterogeneous cells, and function activators or inhibitors utilizing these sugar chains are expected to provide useful drugs. That is, sialyl Lewis X (SLe$^x$), which is a representative compound, and analogues thereof are considered to be useful for alleviating various diseases accompanied with inflammation by blocking selectin molecules to inhibit the adhesion of lymphocytes to endothelial cells. Further, these sugar chains are considered to participate in adhesion of cancer cells to endothelial cells when the cancer cells undergo blood circulatory metastasis or adhesion of microorganisms to target cells when the microorganisms infect to the target cells, and therefore attached importance as a raw material for developing drugs for suppressing these diseases.

The oligosaccharides having an N-acetyllactosamine structure as their skeleton and derivatives thereof are expected to play an important role in the development of novel drugs and in the research of physiological activity in vivo. If there is obtained an N-acetyllactosamine oligosaccharide, which is their basic skeleton, in particular a long chain N-acetyllactosamine oligosaccharide similar to natural-occurring ligand sugar chains of selectin family, it is considered possible to synthesize the ligand sugar chains of selectin family, which occurs in a trace amount in a natural state, by adding properly a sialic acid residue, a fucosyl residue, a sulfate group, ceramide or the like to the N-acetyllactosamine oligosaccharide.

Further, stable supply of N-acetyllactosamine oligosaccharides, in particular long chain N-acetyllactosamine oligosaccharides, is desired. However, oligosaccharides that have N-acetyllactosamine structure as their skeleton exist only in a trace amount in a natural state and it is very difficult to synthesize long chain N-acetyllactosamine oligosaccharides so that a method for producing N-acetyllactosamine oligosaccharides on an industrial scale and at low costs is desired.

Also, sulfated N-acetyllactosamine oligosaccharides, in particular long chain sulfated N-acetyllactosamine oligosaccharides, are useful as intermediates for the synthesis of N-acetyllactosamine oligosaccharides, in particular long chain N-acetyllactosamine oligosaccharides and, hence, it is expected that provision of a method for producing such oligosaccharides will lead to stable supply of N-acetyllactosamine oligosaccharides.

DISCLOSURE OF THE INVENTION

The present invention has been made from the above-described viewpoints, and its object is to provide a novel N-acetyllactosamine oligosaccharide which serves as a raw material for the synthesis of the ligand sugar chains of selectin family, a novel method for producing an N-acetyllactosamine oligosaccharide, and a novel method for producing a sulfated N-acetyllactosamine oligosaccharide.

As a result of intensive investigation by the present inventors with view to achieving the above-described object, it has now been found that an N-acetyllactosamine oligosaccharide (in particular a long chain N-acetyllactosamine oligosaccharide) can be obtained by adjusting the sulfate group content of keratan sulfate having an N-acetyllactosamine structure as a basic skeleton, enzymatically degrading the keratan sulfate with the thus adjusted sulfate group content to sulfated N-acetyllactosamine oligosaccharides, and then completely desulfating the sulfated N-acetyllactosamine oligosaccharides. The present invention has been completed based on this finding.

It has also been found that a sulfated N-acetyllactosamine oligosaccharide (in particular a long chain sulfated N-acetyllactosamine oligosaccharide) can be obtained by adjusting the sulfate group content of keratan sulfate and enzymatically digesting the keratan sulfate with the adjusted sulfate group content and the present invention has been completed based on this finding.

Further, it has been successful in obtaining a novel N-acetyllactosamine oligosaccharide, which has led to the present invention.

Thus, the present invention provides a method for producing an N-acetyllactosamine oligosaccharide, comprising the steps of: adjusting a sulfate group content of keratan sulfate, allowing an enzyme having an activity to cleave a glycosidic linkage of keratan sulfate (herein sometimes referred to simply as "keratan sulfate-degrading enzyme") to act on the keratan sulfate with the adjusted sulfate group content to obtain a sulfated N-acetyllactosamine oligosaccharide, and then completely desulfating the sulfated N-acetyllactosamine oligosaccharide (herein sometimes referred to simply as "method 1 of the present invention"), and a novel N-acetyllactosamine oligosaccharide (herein sometimes referred to simply as "oligosaccharide of the present invention").

Also, the present invention provides a method for producing a sulfated N-acetyllactosamine oligosaccharide, comprising at least the steps of: adjusting a sulfate group content of keratan sulfate, and allowing one or more enzymes belonging to any one of the enzyme groups of three types of keratan sulfate-degrading enzymes each having a different substrate specificity depending on presence or absence of a sulfate group to act on the keratan sulfate with the adjusted sulfate group content (herein sometimes referred to simply as "method 2 of the present invention"). Note that sometimes the methods 1 and 2 of the present invention are collectively referred to simply as "method of the present invention".

The term "N-acetyllactosamine" as used herein refers to a structure (Gal-GlcNAc) containing a galactose residue (Gal) and an N-acetylglucosamine residue (GlcNAc) linked through a glycosidic linkage. Also, the term "N-acetyllactosamine" as used herein includes a structure (GlcNAc-Gal) containing an N-acetylglucosamine residue (GlcNAc) and a galactose residue (Gal) are linked through a glycosidic linkage.

The term "N-acetyllactosamine oligosaccharide" as used herein refers to an oligosaccharide having at least one N-acetyllactosamine structure, and includes, for example, N-acetyllactosamine itself and oligosaccharides containing N-acetyllactosamine units linked one after another repeatedly through a glycosidic linkage. Also, a sialic acid residue may be added to its non-reducing ends. The non-reducing end and reducing end may be either a galactose residue or an N-acetylglucosamine residue. These are both embraced by the term "N-acetyllactosamine oligosaccharide" used herein. That is, the oligosaccharides represented by the following general formulae (1) to (6) are encompassed by the "N-acetyllactosamine oligosaccharide" used herein:

$(GlcNAc-Gal)_n$ (1)

$SA-Gal-(GlcNAc-Gal)_m$ (2)

$(Gal-GlcNAc)_n$ (3)

$SA-(Gal-GlcNAc)_m$ (4)

$Gal-(GlcNAc-Gal)_n$ (5)

$GlcNAc-(Gal-GlcNAc)_n$ (6)

wherein, Gal represents a galactose residue, GlcNAc represents an N-acetylglucosamine residue, SA represents a sialic acid residue, - represents a glycosidic linkage, n is an integer of 1 to 6, and m is an integer of 1 to 10.

The term "sulfated N-acetyllactosamine oligosaccharide" as used herein refers to an N-acetyllactosamine oligosaccharide having a sulfate group.

The term "sulfated oligosaccharide" as used herein refers to an oligosaccharide having a sulfate group.

The term "adjusting a sulfate group content" as used herein refers to increasing a sulfate group content (i.e., sulfating), decreasing a sulfate group content (i.e., partially desulfating), and unchanging a sulfate group content if a desired sulfate group content has already been reached without further increasing or decreasing it.

The term "partially desulfating" as used herein refers to removing partially sulfate groups and differs from "completely desulfating" in that the former allows a part of sulfate groups to remain.

The term "completely desulfating" as used herein refers to removing substantially all the sulfate groups, thus differing from partially removing sulfate groups.

BEST MODE FOR CARRYING OUT THE INVENTION

1. Method of the present invention

The method 1 of the present invention is a method for producing an N-acetyllactosamine oligosaccharide, which comprises the steps of: adjusting a sulfate group content of keratan sulfate, allowing a keratan sulfate-degrading enzyme to act on the keratan sulfate with the adjusted sulfate group content to obtain a sulfated N-acetyllactosamine oligosaccharide, and then completely desulfating the sulfated N-acetyllactosamine oligosaccharide.

The method 2 of the present invention is a method for producing a sulfated N-acetyllactosamine oligosaccharide, which comprises the steps of: adjusting a sulfate group content of keratan sulfate, and allowing one or more enzymes belonging to any one of the enzyme groups of three types of keratan sulfate-degrading enzymes each having a different substrate specificity depending on presence or absence of a sulfate group to act on the keratan sulfate with the adjusted sulfate group content.

Hereafter, the technology involved in each step of the method of the present invention will be described in detail. Items (1) to (5) described below are technologies common to both the methods 1 and 2 of the present invention and items (6) and (7) are related to the method 1 of the present invention.

(1) Keratan sulfate used in the method of the present invention Keratan sulfate is a glycosaminoglycan having as a repeating unit a disaccharide (i.e., N-acetyllactosamine; LacNAc) consisting of a galactose residue (Gal) and an N-acetylglucosamine residue (GlcNAc) linked through a glycosidic linkage and having a sulfate group in a ratio of 1 to 2 moles of sulfate group per mole of the disaccharide. The sulfate group content of keratan sulfate differs depending on animal species and organ. Usually, keratan sulfate is produced from raw materials, for example, cartilage, bones, corneas, etc., of cartilaginous fish such as shark, and mammals such as whales and oxen. The keratan sulfate that can be used in the method of the present invention may be any generally available one and is not limited to a particular one. However, it is preferred to use a highly sulfated keratan sulfate in which galactose residues of constituent sugars are sulfated (highly sulfated keratan sulfate containing 1.5 to 2 moles of sulfate group per mole of the constituent disaccharide is sometimes referred to as keratan polysulfate). Sulfate groups are attached to the galactose residue preferably at the 6-position. Such a highly sulfated keratan sulfate can be obtained, for example, from proteoglycan of the cartilage of cartilaginous fish such as shark. Alternatively, commercially available ones may also be used. The term "keratan sulfate" as used herein includes highly sulfated keratan sulfate and keratan polysulfate unless otherwise indicated.

(2) Adjustment of the sulfate group content of keratan sulfate

The method for adjusting the sulfate group content of keratan sulfate includes sulfating and partially desulfating until a desired sulfate group content is reached, and unchanging a sulfate group content if a desired sulfate group content has already been reached without further increasing or decreasing it. One having ordinary skill in the art may select the method for adjusting the sulfate group content appropriately depending the sulfate group content of keratan sulfate to be used in the method of the present invention, the type of keratan sulfate-degrading enzyme to be used in the method of the present invention, and the target size of an oligosaccharide.

The sulfate group content is adjusted to such an extent that oligosaccharides having a target molecular size can be obtained by the action of a keratan sulfate-degrading enzyme and more specifically, to an extent that sulfate groups are present in a ratio of 0.3 to 1.5 moles on average per mole of the constituent disaccharide.

When an enzyme selected from the group consisting of the enzyme groups (1) and (2) as explained in detail below is used as the keratan sulfate-degrading enzyme, it is preferred to use keratan sulfate having a sulfate group content which has been adjusted such that a sulfate group is present in a ratio of 1.1 to 1.5 moles per mole of the constituent disaccharide. Also, when an enzyme selected from the group consisting of the enzyme groups (2) and (3) as explained in detail below is used as the keratan sulfate-degrading enzyme, it is preferred to use keratan sulfate having a sulfate group content which has been adjusted such that a sulfate group is present in a ratio of 0.3 to 0.8 mole per mole of the constituent disaccharide.

Hereafter, the method for adjusting a sulfate group content of keratan sulfate will be described.

(2-1) Partial desulfation

Partial desulfation may be performed by a known method for desulfation of glycosaminoglycan. However, it is necessary to set up the reaction conditions such as the temperature and time of desulfation reaction, and the concentration of a desulfating agent and the like lest substantially all the sulfate groups should be removed. More particularly, the temperature and time of desulfation reaction as well as the concentration of a desulfating agent and the like are set up at lower values than the reaction conditions at which substantially all the sulfate groups are removed. One skilled in the art may appropriately select specific reaction conditions depending on the keratan sulfate to be used, type of the keratan sulfate-degrading enzyme to be used in cleaving the glycosidic linkages of keratan sulfate with an adjusted sulfate group content, target molecular size (molecular weight, number of sugar chains) of N-acetyllactosamine oligosaccharide and the like.

The known method for desulfation of glycosaminoglycan includes, for example, acid hydrolysis, alkaline decomposition, and heating in an organic solvent (Method in Carbohydrate Chemistry, vol. VIII, p281–289 (1980)). That is, as the desulfating agent, there can be used an acid, an alkali, an organic solvent and the like.

In the case of acid hydrolysis, for example, there can be used as the acid, an inorganic acid, an organic acid, a highly acidic cation exchange resin, and a particularly sulfonated resin. As the reaction solvent, there can be used water, methanol and the like. In the method of the present invention, it is preferred to use anhydrous methanol solution containing acetyl chloride.

In the case of using an organic solvent, for example, the organic solvent may be an aprotic solvent such as dimethyl sulfoxide (DMSO), N,N-dimethylformamide (DMF), and pyridine. When DMSO is used, a method in which keratan sulfate pyridinium salt is heated at 20 to 100° C. in a DMSO solution containing 5 to 10% of water or methanol is widely used (Shin Seikagaku Jikken Koza, vol. 3, Toshitsu II, Tokyo Kagaku Dojin, p325–326 (1989)) and it is preferred to use this method in the method of the present invention.

Also, a desulfation method in which a silylating agent is used may be employed.

Japanese Patent Application Laid-open No. 5-230090 (1993) discloses a method for producing a desulfated sugar in which an organic base salt of a sulfated sugar is reacted with an N,O-bis(trimethylsilyl)acetamide in the presence of the organic base to selectively desulfate sulfate groups attached to primary hydroxyl groups of the sulfated sugar. This method may also be used in the method of the present invention.

First, keratan sulfate is dissolved in an organic base as a solvent to form an organic base salt of keratan sulfate.

Examples of the organic base salt of keratan sulfate include salts of aromatic amines such as pyridine, dimethylaniline, and diethylaniline; of tertiary amines such as trimethylamine, triethylamine, tributylamine, N,N-diisopropylethylamine, trioctylamine, and N,N,N',' -tetramethyl-1,8-naphthalenediamine; and of N-alkyl heterocyclic amines such as N-methylpyrimidine, N-ethylpyrimidine, N-methylmorpholine, and N-ethylmorpholine.

Subsequently, desulfation can be carried out at a reaction temperature of room temperature to 100° C. in the presence of anhydrous organic base with adding a trimethylsilylating agent such as N,O-bis(trimethylsilyl)acetamide (BTSA), N,O-bis(trimethylsilyl)trifluoroacetamide (BTSFA), N,O-bis(trimethylsilyl)difluoroacetamide, N,O-bis(trimethylsilyl)monofluoroacetamide or the like.

Japanese Patent Application Laid-open No. 7-62001 (1995) discloses a method for producing a desulfated sugar characterized by subjecting a sulfated sugar to desulfation reaction in the presence of a silylating agent represented by the general formula (A):

$$CH_3—C[—OSi(R)_3]=CH—COCH_3 \qquad (A)$$

wherein, R, which may be the same or different, represent independently an alkyl group or an aryl group. This method may also be used in the method of the present invention. Even in this method, it is preferred to allow the silylating agent represented by general formula (A) above to react with the organic base salt of sulfated sugar. As the organic base salt, there can be used the same organic base salts as described in Japanese Patent Application Laid-open No. 5-230090 (1993) supra. Examples of $(R)_3SiO$ in general formula (A) above include trimethylsilyloxy, triethylsilyloxy, dimethylisopropylsilyloxy, isopropyldimethylsilyloxy, methyldi-t-butylsilyloxy, t-butyldimethylsilyloxy, t-butyldiphenylsilyloxy, and triisopropylsilyloxy. The most preferred silylating agent represented by the general formula (A) above is 2-trimethylsiloxypent-2-en-4-on. Desulfation can be performed by conducting reaction at room temperature to 100° C.

International Publication (WO96/01278) discloses a method for producing a desulfated polysaccharide characterized by selectively desulfating sulfate groups attached to the primary hydroxyl groups of the polysaccharide by allowing a silylating agent represented by the general formula (B):

$$(R^1)_3C—C(=O)N(—R^2)—Si(R^3)_3 \qquad (B)$$

wherein, $R^1$, which may be the same or different, represent independently a hydrogen atom or a halogen atom, $R^2$ represents a lower alkyl group, and $R^3$, which may be the same or different, represent independently a lower alkyl group, an aryl group, or a halogen atom, to react therewith. This method is also usable in the method of the present invention. In this method too, it is preferred to react the silylating agent represented by the above-described formula with the organic base salt of sulfated sugar. As the organic base salt of sulfate sugar, there can be used the same organic base salts as described in Japanese Patent Application Laid-open No. 5-230090 (1993) supra. As the silylating agent, there can be used those represented by general formula (B) above in which $R^1$, which may be the same or different, represent independently a hydrogen atom or a halogen atom such 2 as fluorine, R represents a lower alkyl group having 1 to 6 carbon atoms, such as a methyl group, an ethyl group, a propyl group, an isopropyl group, a butyl group, an isobutyl group, a sec-butyl group, a tert-butyl group, a pentyl group, an isopentyl group, and a hexyl group, and R³, which may be the same or different, represent independently the same lower alkyl group as describe above, an aryl group such as a phenyl group, or a halogen atom such as chlorine or fluorine. Examples of (R³)₃Si in general formula (B) above include trimethylsilyl, triethylsilyl, dimethylisopropylsilyl, isopropyldimethylsilyl, methyldi-t-butylsilyl, t-butyldimethylsilyl, t-butyldiphenylsilyl, and tri-isopropylsilyl. Most preferred silylating agents represented by general formula (B) above include N-methyl-N-trimethylsilylacetamide (MTMSA) and N-methyl-N-trimethylsilyltrifluoroacetamide (MTSTFA). Desulfation can be performed by conducting reaction at room temperature to 100° C.

Furthermore, an enzyme having an activity to desulfate keratan sulfate may be used.

Appropriately setting up reaction conditions in the known methods for desulfating glycosaminoglycan can give rise to keratan sulfate with the amount of sulfate group reduced to a suitable level.

(2-2) Sulfation

Sulfation can be carried out by a known method for sulfating glycosaminoglycan and is not limited to a particular method. For example, there can be cited the method disclosed in Japanese Patent Application Laid-open No. 61-47701 (1986). AS stated above, keratan sulfate generally has a high sulfate group content and therefore it is mostly the case that the sulfate group content of keratan sulfate is adjusted by partial desulfation. However, when keratan sulfate or the like that has an extremely low sulfate group content is available and usable, the sulfate group content may be adjusted by sulfation. When sulfation is used for adjusting the sulfate group content, it is preferred to sulfate only the 6-position of a galactose residue and/or N-acetylglucosamine residue, so that it is preferred to select a sulfation method that is specific to the 6-position.

Also, an enzyme which transfers a sulfate group specifically to the 6-position of galactose residue and/or N-acetylglucosamine residue of keratan sulfate (sulfotransferase) may be used.

The sulfate group content of keratan sulfate or that with an adjusted sulfate group content can be determined by a known method and evaluated, for example, based on the results obtained by allowing a keratan sulfate-degrading enzyme thereon. Alternatively, it can be evaluated based on the mole number of sulfate group per mole of the constituent disaccharide. The mole number of sulfate group per mole of the constituent disaccharide can be determined by determining galactose or N-acetylglucosamine by an anthrone method or aminosugar analysis to obtain number of sugar residues, determining a sulfate group content by ion chromatography of hydrochloric acid decomposition product of a sugar, and calculating from these values. If the keratan sulfate used as a raw material has a desired sulfate group content, there is no need for conducting adjustment of the sulfate group content (i.e., sulfation or partial desulfation) positively but the keratan sulfate can be used as it is in the invention.

In the method of the present invention, since keratan sulfate generally has a high sulfate group content and it is preferred to use highly sulfated keratan sulfate or keratan polysulfate or for some other reasons, the adjustment of a sulfate group content of keratan sulfate in the method of the present invention is in many cases carried out by partial desulfation, which is preferred. It is preferred to accordingly select a keratan sulfate-degrading enzyme (described later on).

(3) Keratan sulfate-degrading enzyme used in the method of the present invention The keratan sulfate-degrading enzyme that can be used in the method of the present invention is not limited to a particular one as far as it is an enzyme that has an activity to cleave the glycosidic linkage of keratan sulfate. However, it is preferred to use one or more enzymes belonging to any one of enzyme groups (1) to (3) below.

Enzyme group (1): Enzymes having the following activity and substrate specificity:

(a) Activity:

The enzyme cleaves a β-galactosidic linkage of keratan sulfate.

(b) Substrate specificity:

- If a galactose residue participating in the β-galactosidic linkage has a sulfate group at its 6-position, the enzyme does not act on the β-galactosidic linkage.

Whether or not a sulfate group is present at 6-position of an N-acetylglucosamine residue adjacent to a non-reducing end of a galactose residue participating in the β-galactosidic linkage and having no sulfate group at its 6-position, the enzyme acts on the β-galactosidic linkage.

The enzyme group (1) preferably comprises endo-β-galactosidases.

The enzymes of the enzyme group (1) include, for example, an endo-β-galactosidase from *Escherichia freundii* (H. Nakagawa, T. Yamada, J- L. Chien, A. Gardas, M. Kitamikado, S- C. Li, Y- T. Li, J. Biol. Chem., 255, 5955 (1980); herein sometimes referred to simply as "E-Galase"), which is preferred.

Enzyme group (2): Enzymes having the following activity and substrate specificity:

(a) Activity:

The enzyme cleaves a β-galactosidic linkage of keratan sulfate.

(b) Substrate specificity:

If a galactose residue participating in the β-galactosidic linkage has a sulfate group at its 6- position, the enzyme does not act on the β-galactosidic linkage.

If a sulfate group is present at 6-position of an N-acetylglucosamine residue adjacent to a non-reducing end of a galactose residue participating in the β-galactosidic linkage and having no sulfate group at its 6-position, the enzyme acts on the β-galactosidic linkage.

If a sulfate group is absent at the 6-position of the N-acetylglucosamine residue adjacent to the non-reducing end of the galactose residue participating in the β-galactosidic linkage and having no sulfate group at its 6-position, the enzyme does not act on the β-galactosidic linkage.

The enzyme group (2) preferably comprises endo-β-galactosidases.

The enzymes of the enzyme group (2) include, for example, an endo-β-galactosidase from Pseudomonas sp. IFO-13309 (K. Nakazawa, N. Suzuki, S. Suzuki, J. Biol. Chem., 250, 905 (1975); K. Nakazawa, S. Suzuki, J. Biol. Chem., 250, 912 (1975)) and an endo-β-galactosidase produced by Pseudomonas reptilivora disclosed in Japanese Patent Publication No. 57-41236 (1982) (herein these enzymes are sometimes referred to simply as "keratanase" or "KSase"), which are preferred.

Enzyme group (3): Enzymes having the following activity and substrate specificity:

(a) Activity:

The enzyme cleaves a β-N-acetylglucosaminidic linkage of keratan sulfate.

(b) Substrate specificity:

If sulfate groups are present at 6-position of an N-acetylglucosamine residue participating in the β-N-acetylglucosaminidic linkage and at 6-position of a galactose residue adjacent to a non-reducing end of the N-acetylglucosamine residue, respectively, the enzyme acts on the β-N-acetylglucosaminidic linkage.

If a sulfate group is present at the 6-position of the N-acetylglucosamine residue participating in the β-N-acetylglucosaminidic linkage but it is absent at the 6-position of the galactose residue adjacent to the non-reducing end of the N-acetylglucosamine residue, the enzyme acts on the β-N-acetylglucosaminidic linkage.

If a sulfate group is present neither at the 6-position of the N-acetylglucosamine residue participating in the β-N-acetylglucosaminidic linkage nor at the 6-position of the galactose residue adjacent to the non-reducing end of the N-acetylglucosamine residue, the enzyme does not act on the β-N-acetylglucosaminidic linkage.

The enzyme group (3) preferably comprises endo-β-N-acetylglucosamidase.

The enzymes of the enzyme group (3) include, for example, an endo-β-N-acetylglucosamidase from Bacillus sp. Ks36 (Shinichi Hashimoto, Kiyoshi Morikawa, Hiroshi Kikuchi, Keiichi Yoshida, Kiyochika Tokuyasu, Seikagaku, 60, 935 (1988); herein sometimes referred to simply as "keratanase II" or "KSase II") and an endo-β-N-acetylglucosamidase from *Bacillus circulans* KsT202 (disclosed in WO96/16166), which are preferred.

Both of the enzyme groups (1) and (2) include endo-β-galactosidase type enzymes but they have different substrate specificities depending on sulfate groups in the sugar chain. The enzyme group (3) includes endo-β-N-acetylglucosaminidase type enzymes. Therefore, the reducing end of an oligosaccharide obtained by enzymatic digestion is a galactose residue (Gal) when an endo-β-galactosidase type enzyme is used or an N-acetylglucosamine residue (GlcNAc) when an endo-β-N-acetylglucosaminidase type enzyme is used.

The substrate specificities of the enzyme groups (1) to (3) are summarized below. It is indicated whether or not the enzyme cleaves a glycosidic linkage represented by "~" in general formulae (a) to (k) below (i.e., β-galactosidic linkage in the case of the enzyme groups (1) and (2) or β-N-acetyl-glucosaminidic linkage in the case of the enzyme group (3)).

TABLE 1

| Enzyme Group (1) | |
| --- | --- |
| (a) . . . GlcNAc-Gal(6S)~GlcNAc . . . | Not cleave |
| (b) . . . GlcNAc(6S)-Gal(6S)~GlcNAc . . . | Not cleave |
| (c) . . . GlcNAc(6S)-Gal~GlcNAc . . . | Cleave |
| (d) . . . GlcNAc-Gal~GlcNAc . . . | Cleave |
| Enzyme Group (2) | |
| (e) . . . GlcNAc-Gal(6S)~GlcNAc . . . | Not cleave |
| (f) . . . GlcNAc(6S)-Gal(6S)~GlcNAc . . . | Not cleave |
| (g) . . . GlcNAc(6S)-Gal~GlcNAc . . . | Cleave |
| (h) . . . GlcNAc-Gal~GlcNAc . . . | Not cleave |
| Enzyme Group (3) | |
| (i) . . . Gal(6S)-GlcNAc(6S)~Gal . . . | Cleave |
| (j) . . . Gal-GlcNAc(6S)~Gal . . . | Cleave |
| (k) . . . Gal-GlcNAc~Gal . . . | Not cleave |

In the above formulae, Gal represents a galactose residue, GlcNAc represents an N-acetylglucosamine residue, (6S) indicates that the hydroxyl group at the 6-position is sulfated, "-" and "~" represent each a glycosidic linkage, and " . . . " represents a structure of Gal and GlcNAc alternately linked through a glycosidic linkage.

(4) Conditions for enzymatic action

Keratan sulfate from cartilage has a high content of a disulfated N-acetyllactosamine (LacNAc-diS) residue. In keratan sulfate from shark, its content is particularly high. Therefore, enzymes of the enzyme groups (1) and (2) (e.g., E-Galase or KSase) do not substantially act on such keratan sulfate. On the contrary, such keratan sulfate is substantially degraded by the enzymes of the enzyme group (3) (e.g., KSase II) and readily converted into disaccharides and tetrasaccharides. However, this keratan sulfate whose sugar chain has been partially desulfated is more susceptible to the action of the enzymes of the enzyme group (1) and (2) but in contrast less susceptible to the action of the enzymes of the enzyme group (3) according as the degree of desulfation increases. Combination of the substrate specificity of the enzymes described above with the degree of partial desulfation of keratan sulfate permits control of the molecular size of an N-acetyllactosamine oligosaccharide to be finally obtained by the method of the present invention. In other words, if the degree of partial sulfation is controlled such that the action of enzyme is increased depending on the specificity of the enzyme used, the molecular size will be decreased. Conversely, if the degree of partial sulfation is controlled such that the action of the enzyme is decreased, the molecular size will be increased.

If the substrate is in small amounts, keratan sulfate with an adjusted sulfate group content and one or more enzymes of any one of the enzyme groups (1) to (3) above may be put together so that the enzyme or enzymes can act on the keratan sulfate. However, when the enzyme treatment is carried out on an large scale, it is preferred that the enzyme or enzymes is or are allowed to act continuously by using immobilized enzyme(s) obtained by binding the enzyme or enzymes to an appropriate solid phase (beads or the like) or a membrane type reactor with an ultrafiltration membrane, a dialysis membrane or the like.

As stated above, a sulfated N-acetyllactosamine oligosaccharide having a desired molecular size can be obtained by appropriately combining the degree of partial desulfation of keratan sulfate and the substrate specificity of a keratan sulfate-degrading enzyme.

(5) Fractionation of sulfated N-acetyllactosamine oligosaccharide

The fractionation of the sulfated N-acetyllactosamine oligosaccharide produced by the action of the enzyme as described above may be performed using conventional techniques for sugar chain separation and purification. For example, the fractionation may be carried out by operations such as adsorption chromatography, anion exchange chromatography, hydrophobic chromatography, gel filtration, gel permeation chromatography, filter paper electrophoresis, filter paper chromatography, fractionation with organic solvents, or combinations of these. However, it is not limited thereto.

It is preferred that the sulfated N-acetyllactosamine oligosaccharide generated by the enzyme treatment be fractionated according to the molecular size of oligosaccharides. The fractionation method according to the molecular size is not limited particularly. For example, there can be cited fractionation methods using gel filtration chromatography with various gel filtration carriers or fractionation methods with organic solvents. The gel filtration carrier is not limited particularly as far as it is a carrier fabricated for molecular sieve and includes crosslinked acrylamide and crosslinked particles of polysaccharides such as dextran, agarose, and cellulose and the like. Also, carriers with a suitable degree of crosslinking may be selected suitably depending on the target molecular size of oligosaccharides. Use of gel filtration chromatography may permit separation according to the molecular size of the respective oligosaccharides as far as oligosaccharides up to octasaccharides are concerned, whereas separability of oligosaccharides having a chain length larger than the octasaccharides may decrease with an increased molecular size of the oligosaccharide. In this case, fractionation gives a mixture of oligosaccharides with several molecular sizes.

The mixture of oligosaccharides may be fractionated preliminarily with an anion exchange resin according to the density of sulfate group. This increases the separability attained by subsequent gel filtration chromatography. Polysulfated oligosaccharides, when they have the same sulfate group density, are adsorbed more strongly on anion exchange resins as their molecular size becomes larger, so that they can be separated from each other based on this principle by controlling the concentration of salts.

In the case of fractionation with an organic solvent, it is preferred to use alcohol or acetone, for example.

The skeletons of sugar chain of the thus obtained sulfated N-acetyllactosamine oligosaccharides are represented by general formulae (1) to (6) below. More specifically, general formulae (1) and (2) below represent the skeletons of sulfated N-acetyllactosamine oligosaccharide obtained when one or more enzymes of the enzyme group (1) and/or (2) is or are allowed to act on the keratan sulfate with an adjusted sulfate group content in the method of the present invention. On the other hand, general formulae (3) and (4) below represent the skeletons of sulfated N-acetyllactosamine oligosaccharide obtained when one or more enzymes of the enzyme group (3) is or are allowed to act on the keratan sulfate with an adjusted sulfate group content in the method of the present invention. Further, general formulae (5) and (6) below represent the skeletons of sulfated N-acetyllactosamine oligosaccharide obtained when one or more enzymes of the enzyme group (1) and/or (2) and one or more enzymes of the enzyme group (3) are allowed to act on the keratan sulfate with an adjusted sulfate group content in the method of the present invention.

$(GlcNAc-Gal)_n$ (1)

$SA-Gal-(GlcNAc-Gal)_m$ (2)

$(Gal-GlcNAc)_n$ (3)

$SA-(Gal-GlcNAc)_m$ (4)

$Gal-(GlcNAc-Gal)_n$ (5)

$GlcNAc-(Gal-GlcNAc)_n$ (6)

In the formulae above, Gal represents a galactose residue, GlcNAc represents an N-acetylglucosamine residue, SA represents a sialic acid residue, - represents a glycosidic linkage, n is an integer of 1 to 6, and m is an integer of 1 to 10.

For example, in the case where keratanase II, which is an enzyme belonging to the enzyme group (3) above, is allowed to act on keratan sulfate with an adjusted sulfate group content in the method of the present invention, sulfated N-acetyllactosamine oligosaccharides having the skeletons represented by the following formulae are obtained:

Gal-GlcNAc-Gal-GlcNAc-Gal-GlcNAc (7)

Gal-GlcNAc-Gal-GlcNAc-Gal-GlcNAc-Gal-GlcNAc (8)

Gal-GlcNAc-Gal-GlcNAc-Gal-GlcNAc-Gal-GlcNAc-Gal-GlcNAc (9)

Gal-GlcNAc-Gal-GlcNAC-Gal-GlcNAc-Gal-GlcNAc-Gal-GlcNAc-Gal-GlcNAC (10)

SA-Gal-GlcNAc-Gal-GlcNAc-Gal-GlcNAc (11)

SA-Gal-GlcNAc-Gal-GlcNAc-Gal-GlcNAc-Gal-GlcNAc (12)

SA-Gal-GlcNAc-Gal-GlcNAc-Gal-GlcNAc-Gal-GlcNAc-Gal-GlcNAc (13)

SA-Gal-GlcNAc-Gal-GlcNAc-Gal-GlcNAc-Gal-GlcNAc-Gal-GlcNAc-Gal-GlcNAc (14)

wherein, Gal represents a galactose residue, GlcNAc represents an N-acetylglucosamine residue, SA represents a sialic acid residue, and - represents a glycosidic linkage.

The sulfated N-acetyllactosamine oligosaccharides having the skeletons represented by the formulae (7) to (14) above are merely specific examples of sulfated N-acetyll actosamine oligosaccharides having the skeletons represented by general formulae (3) and (4) above, and the present invention is not limited thereto.

Complete desulfation of the sulfated N-acetyllactosamine oligosaccharides having the skeletons represented by general formulae (1) to (6) above by the method described below gives rise to N-acetyllactosamine oligosaccharides represented by the following general formulae:

$(GlcNAc-Gal)_n$ (1)

$SA-Gal-(GlcNAc-Gal)_m$ (2)

$(Gal-GlcNAc)_n$ (3)

$SA-(Gal-GlcNAc)_m$ (4)

$Gal-(GlcNAc-Gal)_n$ (5)

$GlcNAc-(Gal-GlcNAc)_n$ (6)

wherein, Gal represents a galactose residue, GlcNAc represents an N-acetylglucosamine residue, SA represents a sialic acid residue, - represents a glycosidic linkage, n is an integer of 1 to 6, and m is an integer of 1 to 10.

For example, complete desulfation of the sulfated N-acetyllactosamine oligosaccharides having the skeletons represented by general formulae (7) to (14) above by the method described below gives rise to N-acetyllactosamine oligosaccharides represented by the following general formulae:

Gal-GlcNAc-Gal-GlcNAc-Gal-GlcNAc (15)

Gal-GlcNAc-Gal-GlcNAc-Gal-GlcNAc-Gal-GlcNAc (16)

Gal-GlcNAc-Gal-GlcNAc-Gal-GlcNAc-Gal-GlcNAc-Gal-GlcNAc (17)

Gal-GlcNAc-Gal-GlcNAc-Gal-GlcNAc-Gal-GlcNAc-Gal-GlcNAc-Gal-GlcNAc (18)

SA-Gal-GlcNAc-Gal-GlcNAc-Gal-GlcNAc (19)

SA-Gal-GlcNAc-Gal-GlcNAc-Gal-GlcNAc-Gal-GlcNAc (20)

SA-Gal-GlcNAc-Gal-GlcNAc-Gal-GlcNAc-Gal-GlcNAc-Gal-GlcNAc (21)

SA-Gal-GlcNAc-Gal-GlcNAc-Gal-GlcNAc-Gal-GlcNAc-Gal-GlcNAc-Gal-GlcNAc (22)

wherein, Gal represents a galactose residue, GlcNAc represents an N-acetylglucosamine residue, SA represents a sialic acid residue, - represents a glycosidic linkage.

The N-acetyllactosamine oligosaccharides represented by the formulae (15) to (22) above are merely specific examples of N-acetyllactosamine oligosaccharides obtainable from sulfated N-acetyllactosamine oligosaccharides having the skeletons represented by general formulae (3) and (4) above, and the present invention is not limited thereto.

In the formulae (1) to (6) above, n is an integer of 1 to 6. However, long chain N-acetyllactosamine oligosaccharides, for example, those in which n is an integer of 3 to 6 are preferred, with those in which n is an integer of 5 or 6 being particularly preferred.

Also, in the formulae (1) to (6) above, m is an integer of 1 to 10. However, long chain N-acetyllactosamine oligosaccharides, for example, those in which m is an integer of 3 to 10 are preferred, with those in which m is an integer of 5 to 10 being particularly preferred.

In the formulae (1) to (22) above, preferred sialic acid residue (SA) is an N-acetylneuraminic acid residue (NeuAc). The glycosidic linkage between a sialic acid residue (SA) and a galactose residue (Gal) adjacent to the reducing end of the sialic acid residue (SA) is preferably an α-2,3 glycosidic linkage or α-2,6 glycosidic linkage. The glycosidic linkage between a galactose residue (Gal) and an N-acetylglucosamine residue (GlcNAc) adjacent to the reducing end of the galactose residue (Gal) is preferably a β-1,4 glycosidic linkage. Further, the glycosidic linkage between an N-acetylglucosamine residue (GlcNAc) and a galactose residue (Gal) adjacent to the reducing end of the N-acetylglucosamine residue (GlcNAc) is preferably a β-1,3 glycosidic linkage. As will be described concerning complete desulfation of a sulfated N-acetyllactosamine oligosaccharide, no report has been made on the conditions of desulfating a sulfated N-acetyllactosamine oligosaccharide having a sialic acid residue, which conditions have been found for the first time by the present inventors. In view of this, those particularly preferred among N-acetyllactosamine oligosaccharides and sulfated N-acetyllactosamine oligosaccharides in the method of the present invention include N-acetyllactosamine oligosaccharides and sulfated N-acetyllactosamine oligosaccharides that have a sialic acid residue (for example, those represented by the formulae (2), (4), (11), (12), (13), (14), (19), (20), (21), (22) among (1) to (22)). (6) Complete desulfation of sulfated N-acetyllactosamine oligosaccharide Complete desulfation of a sulfated N-acetyllactosamine oligosaccharide obtained by enzymatic digestion can be performed according to the method for partially desulfating keratan sulfate described above by setting up desulfation conditions appropriately so that substantially all the sulfate groups are desulfated. The desulfation conditions may vary greatly depending on the position at which sulfate groups are attached, the kind and type of linkage of sugars. In other words, sugar chains could decompose or sulfate groups could remain depending on the temperature and solvent conditions. In particular, when complete desulfation of a sulfated N-acetyllactosamine oligosaccharide having a sialic acid residue is contemplated, too hard desulfation conditions will result in removal of sialic acid residues in addition to substantially complete removal of sulfate groups. To prevent this, it is necessary to set up conditions for complete desulfation while retaining sialic acid residues. There has been no report on such conditions. Therefore, as far as sulfated N-acetyllactosamine oligosaccharides having a sialic acid residue are concerned, the desulfation conditions (that is, conditions for complete desulfation while retaining sialic acid residues) described below have been elucidated for the first time by the present inventors. Accordingly, the present invention includes a method for completely desulfating a sulfated N-acetyllactosamine oligosaccharide having a sialic acid residue while retaining the sialic acid residue.

As the method for complete desulfation of a sulfated N-acetyllactosamine oligosaccharide, there can be cited, for example, acid hydrolysis, alkali decomposition, heating in an organic solvent, a method using a silylating agent, a method using an enzyme, as in the case of partial desulfation of keratan sulfate. However, the reaction conditions are different from those of partial desulfation.

Hereafter, the method for complete desulfation will be described more specifically referring to a "dimethyl sulfoxide method" as an example of the desulfation method using an organic solvent, a "methanol-hydrochloric acid method" as an example of the desulfation method involving acid hydrolysis, and a "trimethylsilylating agent method" as an example of the desulfation method using a silylating agent.
(a) Dimethyl sulfoxide (DMSO) method A sulfated N-acetyllactosamine oligosaccharide is dissolved in water and the solution is passed through a strong cation exchange resin (H type) to remove free sulfate groups. Then the solution is neutralized with pyridine to form pyridinium salt of the sulfated N-acetyllactosamine oligosaccharide. The pyridinium salt is dissolved in a DMSO solution containing 5 to 20% by volume, preferably 10% by volume of water and heated at 70 to 100° C. for 2 to 10 hours, preferably at 100° C. for 5 hours, to perform complete desulfation without causing decomposition of the sugar chain.
(b) Methanol-hydrochloric acid method Hydrogen chloride gas is blown into dry methanol that is substantially free of water to form methanol-hydrochloric acid solution. This solution is diluted with dry methanol to adjust to 0.01 N to 1 N, preferably 0.1 N. Well dried sulfated N-acetyllactosamine oligosaccharide is dispersed in the methanol-hydrochloric acid solution and stirred at 4 to 30° C. for 0.5 to 50 hours, preferably at room temperature for 15 hours, to effect complete desulfation.
(c) Trimethylsilylating agent (TMS) method This method is to desulfate a sulfated N-acetyllactosamine oligosaccharide by heating it together with an N-,O-bis(trimethylsilyl)acetamide (BTSA). For example, N-acetyllactosamine oligosaccharide is dissolved in a pyridine solution and BTSA is added thereto in a ratio of 5 to 16 moles, preferably 10 moles, per mole of sulfate group, followed by reaction at 40 to 90° C. for 0.5 to 3 hours, preferably 80° C. for 1 hour, to effect complete desulfation. The desulfation ratio obtained by this method, according to the study by the present inventors, was confirmed to be freely controllable by varying temperature and treatment time.

Other methods for complete desulfation include, for example, those methods using an acid such as sulfuric acid, an alkali such as sodium hydroxide.

Note that the method for complete desulfation is not limited to those described above.

Complete desulfation of a sulfated N-acetyllactosamine oligosaccharide gives rise to an N-acetyllactosamine oligosaccharide.
(7) Fractionation of N-acetyllactosamine oligosaccharide Fractionation of N-acetyllactosamine oligosaccharide can be carried out by use of conventional techniques of separation and purification of sugar chains as in the above-described fractionation method for sulfated N-acetyllactosamine oligosaccharide. For example, the fractionation may be carried out by operations such as adsorption chromatography, anion exchange chromatography, hydrophobic chromatography, gel filtration, gel permeation chromatography, filter paper electrophoresis, filter paper chromatography, fractionation with organic solvents, or combinations of these. However, it is not limited thereto.

The separation of an N-acetyllactosamine oligosaccharide having a sialic acid residue (sialyl N-acetyllactosamine oligosaccharide) from an N-acetyllactosamine oligosaccharide is not limited to a particular method and may be carried out by ion exchange chromatography. No limitation is posed on the method for separating N-acetyllactosamine oligosaccharides having different molecular sizes from each other. For example, separation by chromatography using a reverse phase base column may be carried out by increasing the concentration of methanol from 0 to 20%.

An N-acetyllactosamine oligosaccharide, which is the oligosaccharide of the present invention, can be produced by the above-described methods. The oligosaccharide of the present invention will be described later on.

The method of the present invention preferably comprises the steps of: adjusting a sulfate group content of keratan sulfate, treating the keratan sulfate having an adjusted sulfate group content with one or more enzymes belonging to the enzyme groups (1) to (3) above to obtain a sulfated N-acetyllactosamine oligosaccharide (step 1), and completely desulfating the sulfated N-acetyllactosamine oligosaccharide (step 2). The step 1 preferably includes the step of fractionating the sulfated N-acetyllactosamine oligosaccharide and the step 2 preferably includes the step of fractionating the N-acetyllactosamine oligosaccharide. These fractionating steps may be included in only one of the steps (1) and (2). However, since fractionation is easier if a sulfate group is present, it is more preferred that the step 1 includes the step of fractionating the sulfated N-acetyllactosamine oligosaccharide. It is particularly preferred that the step 1 includes the step of fractionating the sulfated N-acetyllactosamine oligosaccharide and the step 2 includes the step of fractionating the N-acetyllactosamine oligosaccharide.

When the sulfated N-acetyllactosamine oligosaccharide is produced, partial desulfation or sulfation of keratan sulfate and degradation of keratan sulfate with an adjusted sulfate group content may be carried out simultaneously (for example, in the same reactor) in the case where the enzyme having an activity of cleaving the glycosidic linkage of keratan sulfate will not be deactivated under the conditions for partial desulfation or sulfation of keratan sulfate.

According to the method of the present invention, conventionally obtainable keratan sulfate is partially desulfated in advance based on the substrate specificity of keratan sulfate-degrading enzyme, oligosaccharides having desired molecular sizes can be obtained more efficiently than subjecting keratan sulfate as it is to the action of the above-described enzyme.

By allowing an exo type glycosidase which excises a non-reducing end sugar from an N-acetyllactosamine oligosaccharide to act on the N-acetyllactosamine oligosaccharide represented by the general formulae (1) to (6) produced by the method of the present invention, there can be obtained an N-acetyllactosamine oligosaccharide having the sugar residue number reduced by one. Specific examples thereof will be described below.

Allowing an exo-N-acetylglucosamindase to act on the N-acetyllactosamine oligosaccharides represented by the general formulae (1) and (6), there can be obtained N-acetyllactosamine oligosaccharides represented by the general formulae (23) and (24), respectively.

In the above formulae, Gal represents a galactose residue, GlcNAc represents an N-acetylglucosamine residue, - represents a glycosidic linkage, and n is an integer of 2 to 6.

Allowing an exo-β-galactosidase to act on the N-acetyllactosamine oligosaccharides represented by the general formulae (3) and (5), there can be obtained N-acetyllactosamine oligosaccharides represented by the general formulae (25) and (26), respectively.

In the above formulae, Gal represents a galactose residue, GlcNAc represents an N-acetylglucosamine residue, - represents a glycosidic linkage, and n is an integer of 2 to 6.

Further, optional use of a sialidase, for example, N-acetylneuraminidase, can give rise to an N-acetyllactosamine oligosaccharide free of sialic acid residues.

2. Oligosaccharide of the present invention

The oligosaccharide of the present invention is an oligosaccharide obtained by the method described below and having the following physical and chemical properties:

(1) Method:

A method for producing an N-acetyllactosamine oligosaccharide, which comprises the steps of: adjusting a sulfate group content of keratan sulfate, allowing a keratan sulfate-degrading enzyme having an ability to cleave a glycosidic linkage of keratan sulfate to act on the keratan sulfate with the adjusted sulfate group content to obtain a product, and then completely desulfating the product.

(2) Physical and Chemical Properties:

The galactose residue content measured by an anthrone method is 35 to 50% by weight.

The nitrogen content measured by elemental analysis is 3 to 4% by weight.

The molecular weight measured by mass spectrometry is 1,000 to 2,200.

The adjustment of sulfate group content is performed preferably by partial desulfation.

The above-described method preferably includes at least the following steps 1 and 2:

Step 1:

The step of adjusting a sulfate group content of keratan sulfate, and allowing one or more enzymes belonging to any one of the following enzyme groups (1) to (3) to act on the keratan sulfate with the adjusted sulfate group content to obtain a sulfated oligosaccharide:

Enzyme group (1): Enzymes having the following activity and substrate specificity:

(a) Activity:

The enzyme cleaves a β-galactosidic linkage of keratan sulfate.

(b) Substrate specificity:

If a galactose residue participating in the β-galactosidic linkage has a sulfate group at its 6-position, the enzyme does not act on the β-galactosidic linkage.

Whether or not a sulfate group is present at 6-position of an N-acetylglucosamine residue adjacent to a non-reducing end of a galactose residue participating in the β-galactosidic linkage and having no sulfate group at its 6-position, the enzyme acts on the []-galactosidic linkage.

Enzyme group (2): Enzymes having the following activity and substrate specificity:

(a) Activity:

The enzyme cleaves a β-galactosidic linkage of keratan sulfate.

(b) Substrate specificity:

If a galactose residue participating in the β-galactosidic linkage has a sulfate group at its 6-position, the enzyme does not act on the β-galactosidic linkage.

If a sulfate group is present at 6-position of an N-acetylglucosamine residue adjacent to a non-reducing end of a galactose residue participating in the β-galactosidic linkage and having no sulfate group at its 6-position, the enzyme acts on the β-galactosidic linkage.

If a sulfate group is absent at the 6-position of the N-acetylglucosamine residue adjacent to the non-reducing end of the galactose residue participating in the β-galactosidic linkage and having no sulfate group at its 6-position, the enzyme does not act on the β-galactosidic linkage.

Enzyme group (3): Enzymes having the following activity and substrate specificity:

(a) Activity:

The enzyme cleaves a β-N-acetylglucosaminidic linkage of keratan sulfate.

(b) Substrate specificity:

If sulfate groups are present at 6-position of an N-acetylglucosamine residue participating in the β-N-acetylglucosaminidic linkage and at 6-position of a galactose residue adjacent to a non-reducing end of the N-acetylglucosamine residue, respectively, the enzyme acts on the β-N-acetylglucosaminidic linkage.

If a sulfate group is present at the 6-position of the N-acetylglucosamine residue participating in the β-N-acetylglucosaminidic linkage but it is absent at the 6-position of the galactose residue adjacent to the non-reducing end of the N-acetylglucosamine residue, the enzyme acts on the β-N-acetylglucosaminidic linkage.

If a sulfate group is present neither at the 6-position of the N-acetylglucosamine residue participating in the β-N-acetylglucosaminidic linkage nor at the 6-position of the galactose residue adjacent to the non-reducing end of the N-acetylglucosamine residue, the enzyme does not act on the D-N-acetylglucosaminidic linkage.

Step 2: The step of completely desulfating the sulfated oligosaccharide.

The enzyme belonging to the enzyme group (1) above is preferably an endo-β-galactosidase, for example, an endo-β-galactosidase from *Escherichia freundii* (H. Nakagawa, T. Yamada, J- L. Chien, A. Gardas, M. Kitamikado, S- C. Li, Y- T. Li, J. Biol. Chem., 255, 5955 (1980); herein sometimes referred to simply as "E-Galase"), which is preferred.

The enzyme belonging to the enzyme group (2) is preferably an endo-β-galactosidase, examples of which include an endo-β-galactosidase from Pseudomonas sp. IFO-13309 (K. Nakazawa, N. Suzuki, S. Suzuki, J. Biol. Chem., 250, 905 (1975); K. Nakazawa, S. Suzuki, J. Biol. Chem., 250, 912 (1975)) and an endo-β-galactosidase produced by Pseudomonas reptilivora disclosed in Japanese Patent Publication No. 57-41236 (1982) (herein these enzymes are sometimes referred to simply as "keratanase" or "KSase"), which are preferred.

The enzyme belonging to the enzyme group (3) is preferably an endo-β-N-acetylglucosaminidase, examples of which include an endo-β-N-acetylglucosaminidase from Bacillus sp. Ks36 (Shinichi Hashimoto, Kiyoshi Morikawa, Hiroshi Kikuchi, Keiichi Yoshida, Kiyochika Tokuyasu, Seikagaku, 60, 935 (1988); herein sometimes referred to simply as "keratanase II" or "KSase II") and an endo-β-N-acetylglucosaminidase from *Bacillus circulans* KsT202 (disclosed in WO96/16166), which are preferred.

More preferably, the oligosaccharide of the present invention is one having a sialic acid content of 10 to 20% by weight as measured by a thiobarbituric acid method in addition to the above-described physical and chemical properties.

Further, the present invention provides a novel N-acetyllactosamine oligosaccharide represented by any one of the following general formulae (1) to (6):

(1)

(2)

(3)

(4)

(5)

(6)

wherein, Gal represents a galactose residue, GlcNAc represents an N-acetylglucosamine residue, SA represents a sialic acid residue, - represents a glycosidic linkage, n is an integer of 1 to 6, and m is an integer of 1 to 10, with a proviso that n is other than 1 in the formulae (1) and (3).

The method for producing the oligosaccharide of the present invention is not limited to specific ones as far as the oligosaccharide of the present invention is obtained. However, it is preferred that it is produced by the method of the present invention. The method of the present invention is described in the foregoing.

When the oligosaccharide of the present invention is produced by the method of the present invention, for example, if it is contemplated to obtain the N-acetyllactosamine oligosaccharide represented by the formulae (1) or (2), an endo-β-galactosidase type enzyme (for example, an enzyme belonging to the enzyme group (1) or (2)) may be used in the method of the present invention.

When it is contemplated to obtain the N-acetyllactosamine oligosaccharide represented by the formulae (3) or (4), an endo-β-N-acetylglucosaminidase type enzyme (for example, an enzyme belonging to the enzyme group (3)) may be used in the method of the present invention.

Further, when it is contemplated to obtain the N-acetyllactosamine oligosaccharide represented by the formulae (5) or (6), both of an endo-β-galactosidase type enzyme (for example, an enzyme belonging to the enzyme group (1) or (2)) and an endo-β-N-acetylglucosaminidase type enzyme (for example, an enzyme belonging to the enzyme group (3)) may be used in the method of the present invention.

In the case of the oligosaccharide of the present invention having a sialic acid residue (for example, those represented by the formulae (2) and (4)), the sialic acid residue includes an N-acetylneuraminic acid residue and an N-glycolylneuraminic acid residue. The sialic acid residue is preferably an N-acetylneuraminic acid residue (NeuAc).

In the formulae (1) to (6) above, n is an integer of 1 to 6 (provided that n is other than 1 in the formulae (1) and (3)). However, long chain N-acetyllactosamine oligosaccharides, for example, those in which n is an integer of 3 to 6 are preferred, with those in which n is an integer of 5 or 6 being particularly preferred.

In the formulae (1) to (6) above, m is an integer of 1 to 10. However, long chain N-acetyllactosamine oligosaccharides, for example, those in which m is an integer of 3 to 10 are preferred, with those in which m is an integer of 5 to 10 being particularly preferred.

The glycosidic linkage between a sialic acid residue (SA) and a galactose residue (Gal) adjacent to the reducing end of the sialic acid residue (SA) is preferably an α-2,3 glycosidic linkage or α-2,6 glycosidic linkage. The glycosidic linkage between a galactose residue (Gal) and an N-acetylglucosamine residue (GlcNAc) adjacent to the reducing end of the galactose residue (Gal) is preferably a β-1,4 glycosidic linkage. Further, the glycosidic linkage between an N-acetylglucosamine residue (GlcNAc) and a galactose residue (Gal) adjacent to the reducing end of the N-acetylglucosamine residue (GlcNAc) is preferably a β-1,3 glycosidic linkage. As described concerning complete desulfation of a sulfated N-acetyllactosamine oligosaccharide, no report has been made on the conditions of desulfating a sulfated N-acetyllactosamine oligosaccharide having a sialic acid residue, which conditions have been found for the first time by the present inventors. In view of this, those particularly preferred among N-acetyllactosamine oligosaccharides in the method of the present invention and oligosaccharides of the present invention include N-acetyllactosamine oligosaccharides that have a sialic acid residue (for example, those represented by the formulae (2) and (4) among (1) to (6)).

The sugar composition of the oligosaccharide of the present invention can be analyzed, for example, by an anthrone method (determination of the galactose residue), amino sugar analysis (determination of the N-acetylglucosamine residue), or a thiobarbituric acid method (TBA method; determination of the sialic acid residue). However, it is not limited thereto. Also, the sulfate group content can be analyzed by decomposing the oligosaccharide of the present invention with hydrochloric acid and analyzing by ion chromatography. However, it is not limited to this method. The method for analyzing the molecular size of the oligosaccharide of the present invention is not limited to particular ones. For example, it can be examined by analysis after gel filtration chromatography and oligosaccharide after E-Galase treatment. The sugar chain sequence of the oligosaccharide of the present invention can be examined, for example, by a successive degradation method using glycosidases.

The oligosaccharide of the present invention can be identified using these analytical methods, which methods can be used also for confirming the oligosaccharide of the present invention obtained, for example, by the method of the present invention.

To the oligosaccharide of the present invention may optionally be added, for example, a sialic acid residue, a fucosyl residue, a sulfate group, ceramide or the like. Although these substances may be added by a chemical method, it is preferred that they be added using an enzyme.

For example, addition of a fucosyl residue to the oligosaccharide of the present invention may be achieved by use of fucosyltransferase to transfer a fucosyl residue to the oligosaccharide of the present invention. On this occasion, it is preferred that the fucosyl residue be bonded to the N-acetylglucosamine residue, more preferably through an α-1,3 glycosidic linkage. Therefore, use of fucosyltransferase having such an activity is preferred.

When it is contemplated to add a sialic acid residue to the oligosaccharide of the present invention represented by the formulae (1), (3), (5) or (6) above, sialyltransferase may be used to transfer a sialic acid residue to the oligosaccharide of the present invention. On this occasion, it is preferred that the sialic acid residue be bonded to the galactose residue, more preferably to the galactose residue on the non-reducing end through an α-2,3 glycosidic linkage or an α-2,6 glycosidic linkage. Accordingly, use of sialyltransferase having such an activity is preferred.

Further, when it is contemplated to add a sulfate group to the oligosaccharide of the present invention, sulfotransferase may be used to transfer a sulfate group to the oligosaccharide of the present invention. As the sulfotransferase, there can be mentioned, for example, chondroitin 6-sulfotransferase (J. Biol. Chem., 268 (29), 21968-21974, (1993)).

Also, when addition of ceramide is contemplated, it is preferred to join ceramide to the reducing end of the oligosaccharides of the present invention.

These enzymes, which may be selected appropriately depending on the target oligosaccharide, can be used alone or a plurality of enzymes may be allowed to act simultaneously. Alternatively, a plurality of enzymes may be allowed to act successively.

EXAMPLES

Hereafter, the present invention will be described by examples.

Example 1

<1> Preparation of Sulfated N-Acetyllactosamine Oligosaccharide 1-1. Partial desulfation of keratan sulfate by a methanol-hydrochloric acid method and preparation of sulfated N-acetyllactosamine oligosaccharide Keratan sulfate (hereafter, also referred to as "KS") derived from shark cartilage was one prepared according to a literature (Seikagaku, 33, 746–752 (1961)). This contained 1.7 moles of sulfate group per mole of the constituent disaccharide.

Well dried KS (5 g) was suspended in 1 liter of anhydrous methanol solution containing 5 ml of acetyl chloride (equivalent to 0.06 N HCl), and the suspension was allowed to react at 4° C. with shaking. After 0, 2.5, 5, 10, 20, and 40 hours from the initiation of the reaction, 200 ml each of reaction mixtures were collected. Each sample was centrifuged to collect insolubles, and the insolubles were then dissolved in distilled water. The resulting solution was neutralized with 0.01 N sodium hydroxide, dialyzed, desalted, and concentrated to 50 ml. Then, ethanol was added thereto in an amount of 5 fold by volume to form precipitate, and then, the precipitate was collected. The precipitate was washed successively with ethanol and with ether to collect dry powder. After 0, 2.5, 5, 10, 20, and 40 hours from the initiation of the reaction, the reaction product had a sulfate group in an amount of 1.7, 1.3, 1.2, 1.0, 0.9, and 0.8 mole, respectively, per mole of the constituent disaccharide.

Figure 1:
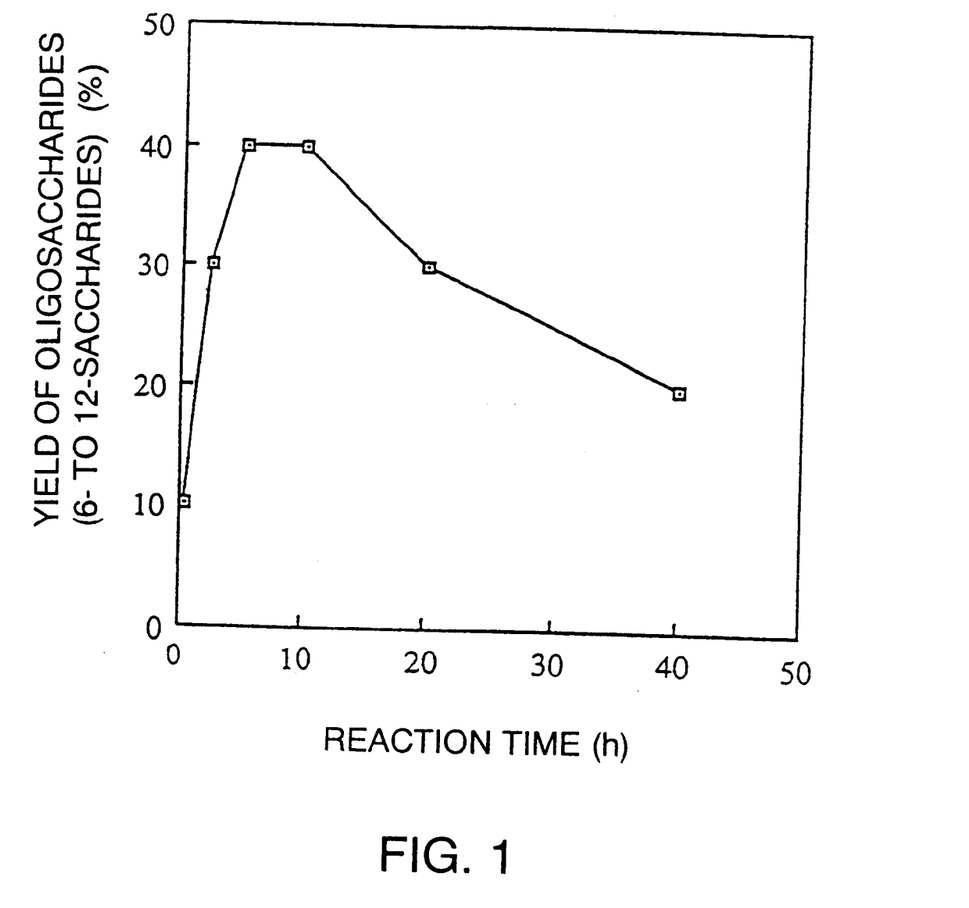
FIG. 1 is a graph illustrating the relationship between the time of partial desulfation of keratan sulfate by a methanol-hydrochloric acid method and the yield of sulfated N-acetyllactosamine oligosaccharides of 6- to 12-saccharides.

To each obtained dry powder (100 mg) was added 10 ml of 20 mM acetate buffer (pH 6.5) to dissolve it. To the solution was added 1 unit of keratanase II (KSase II, manufactured by Seikagaku Corporation; 1 unit (U) is the amount of enzyme that liberates 1 μmole of a reducing group (N-acetylglucosamine) from keratan sulfate (derived from oxen cornea; manufactured by Seikagaku Corporation) at pH 6.5 and at 37° C. for 1 hour.), and enzymatic digestion was carried out at 37° C. for 12 hours. To the solution after the enzymatic digestion, NaCl was added to a final concentration of 0.2 M, and the solution was applied to Cellulofine GCL-9Osf (manufactured by Seikagaku Corporation) column (2×90 cm) and gel filtration was conducted with 0.2 M NaCl. The eluted sulfated N-acetyllactosamine oligosaccharide was detected by an anthrone method (Extra issue, Tanpakushitsu, Kakusan, Koso, Seibutsu Kagaku Jikkenho XI, -Toshitsu Jikkenho-, p.15 (1968), Kyoritsu Shuppan). FIG. 1 illustrates the relationship between the time of partial desulfation of KS by the methanol-hydrochloric acid method and the yield of sulfated N-acetyllactosamine oligosaccharides of 6- to 12-saccharides. The yield of sulfated N-acetyllactosamine oligosaccharides of 6- to 12-saccharides was calculated as a ratio of the area occupied by the fraction corresponding to the sulfated N-acetyllactosamine oligosaccharides of 6- to 12-saccharides to the total area of the figure surrounded by the elution curve of sulfated N-acetyllactosamine oligosaccharides obtained by gel filtration and by the axis of time.

As illustrated in FIG. 1, when partial desulfation of KS was not conducted (that is, the reaction time by the methanol-hydrochloric acid method is 0 hour), the yield of the sulfated N-acetyllactosamine oligosaccharides of 6- to 12-saccharides was about 10%. In contrast, when the partial desulfation of KS by the methanol-hydrochloric acid method was conducted at 4° C. within 40 hours, the yield of the sulfated N-acetyllactosamine oligosaccharides of 6- to 12-saccharides increased about 2 to 4 folds.

In particular, when the time of partial desulfating was 2.5 to 20 hours, the yield was at least about 30% and when the time of partial desulfating was 5 to 10 hours, the yield reached at least about 40%. From this it will be readily understood by those skilled in the art that when it is contemplated to obtain sulfated N-acetyllactosamine oligosaccharides of 6- to 12-saccharides by enzymatic digestion of KS using 1 U of KSase II at 37° C. for 12 hours, the time of partial desulfation of KS by the methanol-hydrochloric acid method at 4° C. is preferably utmost 40 hours (except 0 hour), more preferably 2.5 to 20 hours, and particularly preferably 5 to 10 hours 1-2. Partial desulfation of keratan sulfate by a DMSO method and preparation of sulfated N-acetyllactosamine oligosaccharide A solution of KS (1 g) in water (40 ml) was passed through a column of Dowex 50WX (H$^+$, 100–200 mesh; manufactured by Dow Chemical), and then neutralized with pyridine to form the pyridinium salt, and was lyophilized. The yield of the lyophilized product was 980 mg.

Figure 2:
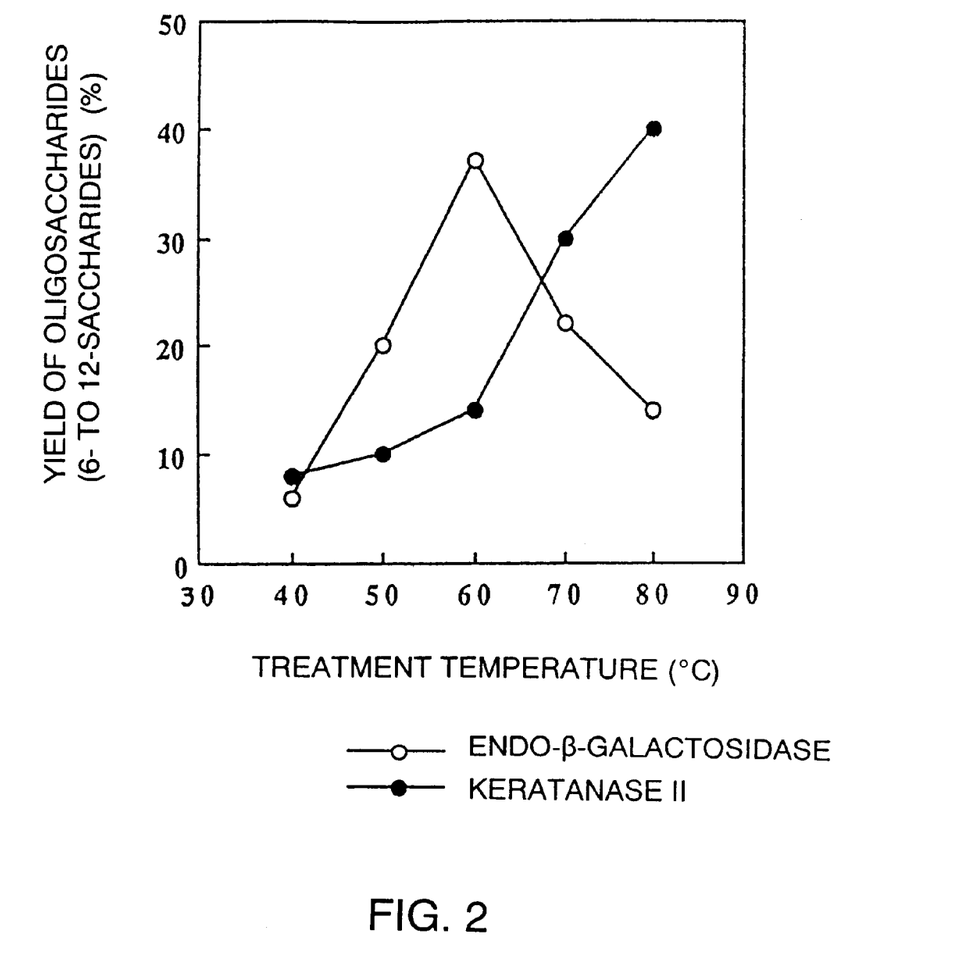
FIG. 2 is a graph illustrating the relationship between the temperature of partial desulfation of keratan sulfate by a DMSO method and the yield of sulfated N-acetyllactosamine oligosaccharides of 6- to 12-saccharides.
Figure 3:
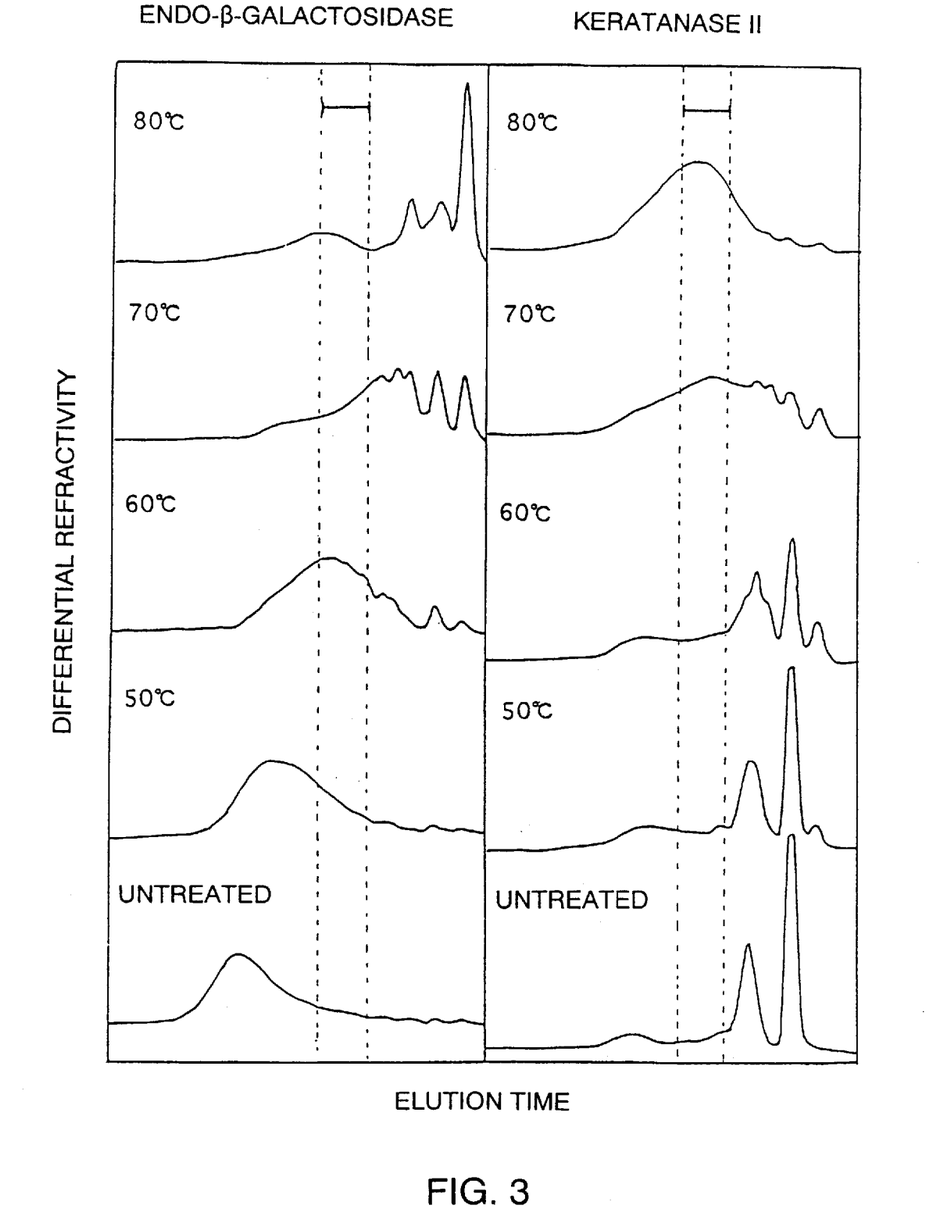
FIG. 3 is an illustration of elution curves of gel filtration of products obtained by allowing endo-β-galactosidase from *Escherichia freundii* or keratanase II to act on keratan sulfate partially desulfated by a DMSO method at various temperatures.

The lyophilized product of KS pyridinium salt (800 mg) was dissolved in 80 ml of 90% DMSO (10% H$_2$O). The resulting solution was divided into four 20 ml-aliquots. Each was allowed to react at 40° C., 50° C., 60° C., 70° C. or 80° C. for 3 hours and then the same volume of water was added to stop the reaction. Each reaction solution was dialyzed in a tap water overnight, concentrated to 4 ml, and then divided into 2 halves by 2 ml. To one of them was added 0.5 ml of 250 mM acetate buffer (pH 6) containing 10 mM calcium acetate and to the other was added 0.5 ml of 100 mM acetate buffer (pH 6.5). After adding an endo-β-galactosidase derived from *Escherichia freundii* (E-Galase, manufactured by Seikagaku Corporation) to the former and KSase II to the latter, each in an amount of 1 U (1 U is the amount of enzyme that liberates a reducing group corresponding to 1 μmole of galactose from keratan sulfate at pH 5.8 and at 37° C. for 1 minute), enzymatic digestion was carried out at 37° C. for 5 hours. The solutions after the enzymatic digestion were subjected to gel filtration in the same manner as in 1-1 above and the resulting sulfated N-acetyllactosamine oligosaccharides were fractionated (FIG. 3). FIG. 2 illustrates the relationship between the temperature of partial desulfation of KS by the DMSO method and the yield of sulfated N-acetyllactosamine oligosaccharides of 6- to 12-saccharides. The yield of sulfated N-acetyllactosamine oligosaccharides of 6- to 12-saccharides was calculated in the same manner as in 1-1 above.

As illustrated in FIG. 2, in the case where an endo-β-galactosidase derived from *Escherichia freundli* is used in the enzymatic digestion, the yield of sulfated N-acetyllactosamine oligosaccharides of 6- to 12-saccharides was at least about 20% when the temperature of Fpartialdesulfation of KS by the DMSO method was about 50 to 70° C., and about 40% when the partial desulfation temperature was 60° C. In the case where KSase II is used in the enzymatic digestion, the yield of sulfated N-acetyllactosamine oligosaccharides of 6- to 12-saccharides are at least about 20% when the temperature of partial desulfation of KS by the DMSO method was at least about 65° C., and reached to 30% when the partial desulfation temperature was 70° C., and about 40% when the partial desulfation temperature was 80° C. From these results, it will be readily understood by those skilled in the art that when it is contemplated to obtain sulfated N-acetyllactosamine oligosaccharides of 6- to 12-saccharides by the enzymatic digestion of KS using 1 U of endo-β-galactosidase derived from *Escherichia freundii* at 37° C. for 5 hours, the temperature at which partial desulfation of KS is performed by the DMSO method for 3 hours is preferably about 50 to 70° C., more preferably 60° C. Also, it will be readily under stood by those skilled in the art that when it is contemplated to obtain sulfated N-acetyllactosamine oligosaccharides of 6- to 12-saccharides by the enzymatic digestion of KS using 1 U of KSase II at 37° C. for 5 hours, the temperature at which partial desulfation of KS is performed by the DMSO method for 3 hours is preferably at least about 65° C., more preferably at least 70° C., and particularly preferably at 80° C.

The reaction products (KS with an adjusted sulfate group content) obtained by partial desulfation of KS by the DMSO method for 3 hours at 40, 50, 60, 70 and 80° C. had a sulfate group in a ratio of 1.6 moles, 1.4 moles, 1.0 mole, 0.8 mole and 0.3 mole, respectively, per mole of the constituent disaccharide.

<2> Complete desulfation of sulfated N-acetyllactosamine oligosaccharide and fractionation of N-acetyllactosamine oligosaccharide 2-1. Complete desulfation of sulfated N-acetyllactosamine oligosaccharide In the same manner as in 1-1 above, dried KS (10 g) was allowed to react with methanol-hydrochloric acid for 10 hours, followed by treatments by KSase II digestion and gel filtration fractionation, and the obtained fractions corresponding to sulfated N-acetyllactosamine oligosaccharides of 6- to 12-saccharides were separated, desalted, lyophilized, and collected. The yield was 3.8 g.

The dry powder (3 g) was suspended in 100 ml of 0.01 N hydrochloric acid-methanol solution and slowly stirred at room temperature for 20 hours. After the reaction was completed, the solution was neutralized with 0.01 N sodium hydroxide, the solvent was removed by evaporation, and then water was added thereto, followed by desalting using a Cellulofine GCL-25 (manufactured by Seikagaku Corporation) column and lyophilizing to obtain N-acetyllactosamine oligosaccharides. The yield was 2.5 g (galactose: 32.4%, sialic acid: 1.8%).

2-2. Fractionation of N-acetyllactosamine oligosaccharide

The lyophilized powder (2 g) of N-acetyllactosamine oligosaccharides obtained in 2-1 above was dissolved in 50 ml of water while heating and the resulting solution was passed through a column of Dowex 1×8 Cl$^-$, 200–400 mesh (3×50 cm; manufactured by Dow Chemical) previously equilibrated with 5 mM NaCl solution and the column was washed with 1 liter of the same solution. Then elution was performed by linear concentration gradient formed by 5 mM to 200 mM NaCl (2 liters), followed by detection of galactose and sialic acid by an anthrone method and a thiobarbituric acid method, respectively, to collect positive fractions. The anthrone-positive fractions in the solution that passed through the column without adsorption were concentrated and subjected to gel filtration using Cellulofine GCL-90sf (manufactured by Seikagaku Corporation) column (4×100 cm) and water as a solvent. The eluate was detected by an anthrone method and peak portions corresponding to 6-, 8-, 10-and 12-saccharides were collected, concentrated, desalted, and lyophilized (The yields were 253 mg for 6-saccharide, 324 mg for 8-saccharide, 185 mg for 10-saccharide, and 54 mg for 12-saccharide). Of these, 100 mg of the 10-saccharide was dissolved in 10 ml of water and the solution was applied to an ODS column, Daiso Pack SP-120-25-ODS-B (manufactured by Daiso Co., Ltd.; 2×50 cm) five times in an amount of 2 ml each time. The column was eluted by use of a concentration gradient system from water to an aqueous 20% methanol solution. Then 10-saccharide fraction was concentrated and lyophilized to collect it. The yield was 78 mg. Similarly, from 100 mg each of 8-saccharide and 6-saccharide fractions were obtained 85 mg and 82 mg of purified powders, respectively.

On the other hand, thiobarbituric acid-positive fractions that had been adsorbed on an absorbent in a Dowex column, eluted with 2 liters of aqueous 5 mM to 200 mM linear concentration gradient NaCl solution, and concentrated were also applied to a Cellulofine GCL-90sf column in the same manner as described above. Each of the fractions were subjected to gel filtration with 0.2 M NaCl solution and fractions corresponding to 9-saccharide, 11-saccharide, and 13-saccharide were collected, and each of them was purified by repeating gel filtration using the same column, desalted, and lyophilized. As a result, sialyl N-acetyllactosamine oligosaccharides of 9-saccharide, 11-saccharide, and 13-saccharide (sialic acid residues are added to the non-reducing ends of N-acetyllactosamine oligosaccharides) were obtained in amounts of 12 mg, 15 mg, and 7 mg, respectively.

Of these, 6-saccharide, 8-saccharide, 10-saccharide, 9-saccharide, 11-saccharide, and 13-saccharide fractions were measured for their sialic acid contents, galactose contents, and nitrogen contents. The sialic acid content, the galactose content, and the nitrogen content were measured by a thiobarbituric acid method, an anthrone method, and elemental analysis, respectively. Table 2 shows the results obtained.

TABLE 2

|  | Sialic acid content (% by weight) | Galactose content (% by weight) | Nitrogen content (% by weight) |
| --- | --- | --- | --- |
| 6-Saccharide | — | 46.2 | 3.53 |
| 8-Saccharide | — | 46.8 | 3.51 |
| 10-Saccharide | — | 46.9 | 3.54 |
| 9-Saccharide | 16.8 | 38.5 | 3.75 |
| 11-Saccharide | 13.4 | 40.1 | 3.72 |
| 13-Saccharide | 11.8 | 41.3 | 3.70 |

(In Table 2, "-" indicates no detection)

Further, mass spectrometric analysis was conducted on the above-described 6-saccharide, 8-saccharide, 10-saccharide, and 11-saccharide fractions. The mass spectrometric analysis was performed by fast atom bombardment mass spectrometry (FAB mass spectrometry). Table 3 shows main peak m/z values read from positive FAB mass spectra and negative FAB mass spectra. Table 3 also shows the molecular weight obtained from mass spectrometric analysis ("Found" in the table) and the molecular weight obtained based on the structural formula ("Calc." in the table).

TABLE 3

|  | Positive FAB Mass (m/z) | Negative FAB Mass (m/z) | Molecular weight | |
| --- | --- | --- | --- | --- |
|  |  |  | Found | Calc. |
| 6-Saccharide | 1114 [M + H]$^+$ 1136 [M + Na]$^+$ | 1112 [M-H]$^-$ | 1113 | 1114 |
| 8-Saccharide | 1479.1[M + H]$^+$ 1501 [M + Na]$^+$ | 1477.3 [M-H]$^-$ | 1478 | 1480 |
| 10-Saccharide | 1844.7[M + H]$^+$ 1865.8[M + Na]$^+$ | 1843.0 [M-H]$^-$ | 1843 | 1845 |
| 11-Saccharide | 2136.7[M + H]$^+$ 2158.8[M + Na]$^+$ 2181.3[M − H + 2Na]$^+$ | 2133.6 [M-H]$^-$ | 2136 | 2136 |

"Found" in Table 3 denotes molecular weights obtained by mass spectrometric analyses.
"Calc." in Table 3 denotes molecular weights obtained based on the following structural formulae.
6-saccharide: (Gal-GlcNAc)$_3$
8-saccharide: (Gal-GlcNAc)$_4$
10-saccharide: (Gal-GlcNAc)$_5$
11-saccharide: NeuAc-(Gal-GlcNAc)$_5$ In the above formulae, Gal represents a galactose residue, GlcNAc represents an N-acetylglucosamine residue, NeuAc represents an N-acetylneuraminic acid residue, and - represents a glycosidic linkage.

The results shown in Table 3 confirmed that the molecular size (molecular weight) of the N-acetyllactosamine oligosaccharide obtained according to the present invention substantially corresponded to the calculated value. Further, it was confirmed that N-acetyllactosamine oligosaccharides with subtle differences in molecular size (molecular weight) could be fractionated depending on the molecular size.

From these results, it is suggested that among those shown in Table 2, the 9-saccharide would be NeuAc-(Gal-GlcNAc)$_4$ and the 13-saccharide would be NeuAc-(Gal-GlcNAc)$_6$.

INDUSTRIAL APPLICABILITY

As described above, the present invention provides novel N-acetyllactosamine oligosaccharides and a novel method for producing N-acetyllactosamine oligosaccharides. The oligosaccharide of the present invention can be utilized as a raw material for synthesizing ligand sugar chains of selectin family that occurs only in trace amounts in the nature. The ligand sugar chains of selectin family are useful for a novel drug, particularly an anti-inflammatory agent.

According to the method 1 of the present invention, the oligosaccharide of the present invention can be produced on an industrial scale and at low costs.

According to the method 2 of the present invention, sulfated N-acetyllactosamine oligosaccharides, which are useful as intermediates for producing the oligosaccharide of the present invention, can be produced on an industrial scale and at low costs. Further, it is possible that the sulfated N-acetyllactosamine oligosaccharides have a novel physiological activity so that their application as a drug is expected.

What is claimed is:

1. A method for producing an N-acetyllactosamine oligosaccharide from keratan sulfate, comprising the steps of:

selecting at least one enzyme having an ability to cleave a specific glycosidic linkage or linkages of keratan sulfate;

changing reactivity of the keratan sulfate against said at least one enzyme by adjusting the sulfate group content of the keratan sulfate in a range effective to obtain a target molecular size of an N-acetyllactosamine oligosaccharide;

allowing said at least one enzyme to act on the keratan sulfate with the adjusted sulfate group content to obtain a sulfated N-acetyllactosamine oligosaccharide; and completely desulfating said sulfated N-acetyllactosamine oligosaccharide to obtain an N-acetyllactosamine oligosaccharide having the target molecular size.

2. The method according to claim 1, wherein said at least one enzyme is selected from the group consisting of:

Enzyme group (1): Enzymes having the following activity and substrate specificity:
(a) Activity:
The enzyme cleaves a β-galactosidic linkage of keratan sulfate;
(b) Substrate specificity:
If a galactose residue participating in the β-galactosidic linkage has a sulfate group at its 6-position, the enzyme does not act on the β-galactosidic linkage;
Whether or not a sulfate group is present at 6-position of an N-acetylglucosamine residue adjacent to a non-reducing end of a galactose residue participating in the β-galactosidic linkage and having no sulfate group at its 6-position, the enzyme acts on the β-galactosidic linkage;

Enzyme group (2): Enzymes having the following activity and substrate specificity:
(a) Activity:
The enzyme cleaves a β-galactosidic linkage of keratan sulfate;
(b) Substrate specificity:
If a galactose residue participating in the β-galactosidic linkage has a sulfate group at its 6-position, the enzyme does not act on the β-galactosidic linkage;
If a sulfate group is present at 6-position of an N-acetylglucosamine residue adjacent to a non-reducing end of a galactose residue participating in the β-galactosidic linkage and having no sulfate group at its 6-position, the enzyme acts on the β-galactosidic linkage;
If a sulfate group is absent at 6-position of the N-acetylglucosamine residue adjacent to the non-reducing end of the galactose residue participating in the β-galactosidic linkage and having no sulfate group at its 6-position, the enzyme does not act on the β-galactosidic linkage; and Enzyme group (3): Enzymes having the following activity and substrate specificity:
(a) Activity:
The enzyme cleaves a β-N-acetylglucosaminidic linkage of keratan sulfate;
(b) Substrate specificity:
If a sulfate groups are present at 6-position of an N-acetylglucosamine residue participating in the β-N-acetylglucosaminidic linkage and at 6-position of a galactose residue adjacent to a non-reducing end of the N-acetylglucosamine residue, respectively, the enzyme acts on the β-N-acetylglucosaminidic linkage;
If a sulfate group is present at the 6-position of the N-acetylglucosamine residue participating in the β-N-acetylglucosaminidic linkage but it is absent at the 6-position of the galactose residue adjacent to the non-reducing end of the N-acetylglucosamine residue, the enzyme acts on the β-N-acetylglucosaminidic linkage;
If a sulfate group is present neither at the 6-position of the N-acetylglucosamine residue participating in the β-N-acetylglucosaminidic linkage nor at the 6-position of the galactose residue adjacent to the non-reducing end of the N-acetylglucosamine residue, the enzyme does not act on the β-N-acetylglucosaminidic linkage.

3. The method for producing an N-acetyllactosamine oligosaccharide according to claim 2, wherein said enzyme reaction step further comprises separating a sulfated N-acctyllactosamine oligosaccharide by fractionation and said desulfation step further comprises separating an N-acetyllactosamine oligosaccharide by fractionation.

4. The method for producing an N-acetyllactosamine oligosaccharide according to claim 2, wherein said enzyme belonging to the enzyme group (1) is an endo-β-galactosidase derived from *Escherichia freundii*.

5. The method for producing an N-acetyllactosamine oligosaccharide according to claim 2, wherein said enzyme belonging to the enzyme group (2) is an endo-β-galactosidase derived from Pseudomonas sp.

6. The method for producing an N-acetyllactosamine oligosaccharide according to claim 2, wherein said enzyme belonging to the enzyme group (3) is an endo-β-N-acetylglucosaminidase derived from Bacillus sp. Ks36 or *Bacillus circulans* KsT202.

7. The method for producing an N-acetyllactosamine oligosaccharide according to claim 1, wherein a sugar chain skeleton of said sulfated N-acetyllactosamine oligosaccharide is represented by any one of the following general formulae (1) to (6):

(GlcNAc-Gal)$_n$     (1)

SA-Gal-(GlcNAc-Gal)$_m$     (2)

(Gal-GlcNAc)$_n$     (3)

SA-(Gal-GlcNAc)$_m$     (4)

Gal-(GlcNAc-Gal)$_n$     (5)

GlcNAc-(Gal-GlcNAc)$_n$     (6)

wherein Gal represents a galactose residue, GlcNAc represents an N-acetylglucosamine residue, SA represents a sialic acid residue, - represents a glycosidic linkage, n is an integer of 3 to 6, and m is an integer of 3 to 10.

8. The method for producing an N-acetyllactosamine oligosaccharide according to claim 1, wherein said N-acetyllactosamine oligosaccharide is represented by any one of the following general formulae (1) to (6):

(GlcNAc-Gal)$_n$     (1)

SA-Gal-(GlcNAc-Gal)$_m$     (2)

(Gal-GlcNAc)$_n$     (3)

SA-(Gal-GlcNAc)$_m$     (4)

Gal-(GlcNAc-Gal)$_n$     (5)

GlcNAc-(Gal-GlcNAc)$_n$     (6)

wherein Gal represents a galactose residue, GlcNAc represents an N-acetylglucosamine residue, SA represents a sialic acid residue, - represents a glycosidic linkage, n is an integer of 3 to 6, and m is an integer of 3 to 10.

9. The method for producing an N-acetyllactosamine oligosaccharide according to claim 2, wherein a sugar chain skeleton of said sulfated N-acetyllactosamine oligosaccharide is represented by any one of the following general formulae (1) to (6):

$$(GlcNAc-Gal)_n \quad (1)$$

$$SA-Gal-(GlcNAc-Gal)_m \quad (2)$$

$$(Gal-GlcNAc)_n \quad (3)$$

$$SA-(Gal-GlcNAc)_m \quad (4)$$

$$Gal-(GlcNAc-Gal)_n \quad (5)$$

$$GlcNAc-(Gal-GlcNAc)_n \quad (6)$$

wherein Gal represents a galactose residue, GlcNAc represents an N-acetylglucosamine residue, SA represents a sialic acid residue, - represents a glycosidic linkage, n is an integer of 3 to 6, and m is an integer of 3 to 10.

10. The method for producing an N-acetyllactosamine oligosaccharide according to claim 2, wherein said N-acetyllactosamine oligosaccharide is represented by any one of the following general formulae (1) to (6):

$$(GlcNAc-Gal)_n \quad (1)$$

$$SA-Gal-(GlcNAc-Gal)_m \quad (2)$$

$$(Gal-GlcNAc)_n \quad (3)$$

$$SA-(Gal-GlcNAc)_m \quad (4)$$

$$Gal-(GlcNAc-Gal)_n \quad (5)$$

$$GlcNAc-(Gal-GlcNAc)_n \quad (6)$$

wherein Gal represents a galactose residue, GlcNAc represents an N-acetylglucosamine residue, SA represents a sialic acid residue, - represents a glycosidic linkage, n is an integer of 3 to 6, and m is an integer of 3 to 10.

11. The method according to claim 2, wherein said at least one enzyme is selected from the group consisting of the Enzyme group (3), and said N-acetyllactosamine oligosaccharide is represented by any one of the following general formulae (3) and (4):

$$(Gal-GlcNAc)_n \quad (3)$$

$$SA-(Gal-GlcNAc)_m \quad (4)$$

wherein Gal represents a galactose residue, GlcNAc represents an N-acetylglucosaminc residue, SA represents a sialic acid residue, - represents a glycosidic linkage, n is an integer of 3 to 6, and in is an integer of 3 to 10.

12. The method according to claim 2, wherein said at least one enzyme is selected from the group consisting of the Enzyme group (3), and the sulfate group content of the keratan sulfate is adjusted in a ratio of 0.3 to 0.8 mole per mole of the constituent disaccharide of the keratan sulfate.

13. The method according to claim 1, wherein the keratan sulfate of which sulfate group content is adjusted is a highly sulfated keratan sulfate containing 1.5 to 2 moles of sulfate group per mole of the constituent disaccharide of the keratan sulfate.

14. The method according to claim 1, wherein the sulfate group content of the keratan sulfate is adjusted by desulfating the keratan sulfate.

* * * * *

UNITED STATES PATENT AND TRADEMARK OFFICE
CERTIFICATE OF CORRECTION

PATENT NO. : 6,132,994
DATED : October 17, 2000
INVENTOR(S) : Akira Tawada and Keiichi Yoshida It is certified that error appears in the above-identified patent and that said Letters Patent is hereby corrected as shown below:

Column 26,
Line 14,, delete "N-acctyllactosamine and insert -- N-acetyllactosamine --;

Column 28,
Line 18, delete "N-acetyllactosamainc and insert -- N-acetyllactosamine --;
Line 20, delete "and in is an integer of 3 to 10" and insert -- and m is an integer of 3 to 10 -- .

Signed and Sealed this

Twenty-fifth Day of September, 2001

Attest:

*Nicholas P. Godici*

NICHOLAS P. GODICI
*Attesting Officer*   *Acting Director of the United States Patent and Trademark Office*